United States Patent
Kelner

(10) Patent No.: US 9,717,427 B2
(45) Date of Patent: Aug. 1, 2017

(54) MOTION BASED ESTIMATION OF BIOMETRIC SIGNALS

(71) Applicant: MICROSOFT TECHNOLOGY LICENSING, LLC, Redmond, WA (US)

(72) Inventor: Ilya Kelner, Bothell, WA (US)

(73) Assignee: MICROSOFT TECHNOLOGY LICENSING, LLC, Redmond, WA (US)

( * ) Notice: Subject to any disclaimer, the term of this patent is extended or adjusted under 35 U.S.C. 154(b) by 263 days.

(21) Appl. No.: 14/292,402

(22) Filed: May 30, 2014

(65) Prior Publication Data
US 2015/0342533 A1 Dec. 3, 2015

(51) Int. Cl.
*A61B 5/00* (2006.01)
*G06F 17/00* (2006.01)
(Continued)

(52) U.S. Cl.
CPC ........ *A61B 5/02438* (2013.01); *A61B 5/0245* (2013.01); *A61B 5/1118* (2013.01);
(Continued)

(58) Field of Classification Search
CPC ....... A61B 5/72; A61B 5/7264; A61B 5/0024; A61B 5/0205; G06F 17/10; G06F 17/15; G06F 19/34; G06F 19/345
(Continued)

(56) References Cited

U.S. PATENT DOCUMENTS

| 5,626,140 A | * | 5/1997 | Feldman | .............. G06K 9/6293 |
| | | | | 600/483 |
| 8,475,370 B2 | | 7/2013 | McCombie et al. | |

(Continued)

FOREIGN PATENT DOCUMENTS

| EP | 0733340 A1 | 9/1996 |
| EP | 2520222 A1 | 11/2012 |

(Continued)

OTHER PUBLICATIONS

ISA European Patent Office, International Search Report and Written Opinion Issued in Application No. PCT/US2015/032505, Nov. 10, 2015, WIPO, 11 pages.

(Continued)

*Primary Examiner* — Mary Zeman
*Assistant Examiner* — Marie Archer
(74) *Attorney, Agent, or Firm* — Alleman Hall Creasman & Tuttle LLP

(57) ABSTRACT

A wearable electronic device, comprising a heart rate sensor to determine a heart rate of the user, a motion sensor to detect motion of a user, the motion sensor operated in an initial calibration phase during which the heart rate sensor is detecting the heart rate of the user, and the motion sensor is detecting the motion of the user, the calibration phase being used to compute a correspondence between motion of the user and the heart rate of the user, the motion sensor being operated in a low power phase during which the heart rate sensor is powered down, and a processor configured to run a heart rate estimation module configured to calculate an estimated heart rate of the user based upon the motion of the user and the correspondence between the heart rate of the user and the motion of the user determined in the calibration phase.

19 Claims, 8 Drawing Sheets

(51) Int. Cl.
*G06F 1/32* (2006.01)
*G06F 19/00* (2011.01)
*A61B 5/024* (2006.01)
*A61B 5/0245* (2006.01)
*G06F 17/10* (2006.01)
*A61B 5/11* (2006.01)

(52) U.S. Cl.
CPC ............ *A61B 5/4866* (2013.01); *A61B 5/681* (2013.01); *A61B 5/721* (2013.01); *A61B 5/725* (2013.01); *G06F 1/32* (2013.01); *G06F 17/10* (2013.01); *G06F 19/345* (2013.01); *A61B 2560/0228* (2013.01)

(58) Field of Classification Search
USPC .............. 600/300–301; 702/19, 104; 700/90
See application file for complete search history.

(56) References Cited

U.S. PATENT DOCUMENTS

| | | | |
|---|---|---|---|
| 8,622,922 | B2 | 1/2014 | Banet et al. |
| 2007/0161874 | A1* | 7/2007 | Aerts ................... A61B 5/0205 600/301 |
| 2007/0276200 | A1* | 11/2007 | Ahola ................ A61B 5/02438 600/300 |
| 2008/0234935 | A1* | 9/2008 | Wolf ...................... G01C 21/16 701/472 |
| 2010/0152600 | A1 | 6/2010 | Droitcour et al. |
| 2011/0066041 | A1 | 3/2011 | Pandia et al. |
| 2011/0098583 | A1 | 4/2011 | Pandia et al. |
| 2011/0245633 | A1* | 10/2011 | Goldberg ............... A61B 5/681 600/301 |
| 2011/0301436 | A1 | 12/2011 | Teixeira |
| 2013/0245502 | A1 | 9/2013 | Lange et al. |
| 2013/0324368 | A1* | 12/2013 | Aragones ............. A61B 5/6829 482/8 |

FOREIGN PATENT DOCUMENTS

| | | |
|---|---|---|
| WO | 2012092303 A1 | 7/2012 |
| WO | 2013038296 A1 | 3/2013 |
| WO | 2013121431 A1 | 8/2013 |
| WO | 2013143893 A1 | 10/2013 |

OTHER PUBLICATIONS

Fingas, Jon, "TomTom's new GPS watches track your heart rate without a chest strap (update: US pricing)", http://www.engadget.com/2014/04/03/tomtom-cardio-gps-watches/, Apr. 3, 2014, 10 pages.

Goode, Lauren, "Samsung's New Gear Fit Needs to Work on the "Fit" Part", http://recode.net/2014/04/08/samsungs-new-gear-fit-needs-to-work-on-the-fit-part/, Apr. 8, 2014, 10 pages.

"Samsung Gear Fit, Gear 2 and Gear 2 Neo go on sale worldwide", NDTV Gadgets, http://gadgets.ndtv.com/others/news/samsung-gear-fit-gear-2-and-gear-2-neo-go-on-sale-worldwide-507220, Apr. 11, 2014, 3 pages.

Poeter, Damon, "Meet Simband, Samsung's Next-Gen Health Tracker", http://www.pcmag.com/article2/0,2817,2458663,00.asp, May 28, 2014, 5 pages.

IPEA European Patent Office, Second Written Opinion issued in PCT/US2015/032505, Apr. 18, 2016, WIPO, 5 pages.

IPEA European Patent Office, International Preliminary Report on Patentability Issued in PCT Application No. PCT/US2015/032505, Aug. 26, 2016, WIPO, 6 pages.

\* cited by examiner

MOTION BASED ESTIMATION OF BIOMETRIC SIGNALS

DETAILED DESCRIPTION

Continuous heart rate monitors have been used for many years to measure various lifestyle metrics of a user, such as the number of calories burned per day by the user. An implementation of a heart rate monitor utilizes an optical sensor together with a high powered LED, to measure the user's heart rate based on changes in the reflection of light from the LED off the user's skin. However, the large power consumption of these optical sensors and LEDs makes continuous use impractical when the sensor is incorporated into a battery-powered mobile device.

In an attempt to address this challenge, heart monitoring devices have utilized methods to estimate the heart rate without requiring constant power to the optical sensor. One such method involves taking the historical average value. In such a method, past heart rate values calculated when the optical sensor was powered are averaged and appropriately weighed over time, and this average value is used as a de facto heart rate when the optical sensor is not powered. Another method is a straight line extrapolation. In this method, the last measured heart rate is used while the sensor is unpowered.

However, both methods of estimation described above share a common flaw in that neither can account for the actual changes in the user's heart rate that occur during the period when the optical sensor is not powered. Thus, if the user's heart rate is used to calculate the number of calories burned daily by the user, these "gaps" in the data set may leave out crucial information and lead to inaccurate or misleading results.

In an exemplary implementation, a wearable electronic device may comprise a heart rate sensor configured to determine a heart rate of the user, and a motion sensor configured to detect motion of a user. The wearable electronic device may operate in an initial calibration phase during which the heart rate sensor is powered and detecting the heart rate of the user, and the motion sensor is detecting the motion of the user. The calibration phase is used to compute a correspondence between motion of the user and the heart rate of the user. The motion sensor also may be operated in a low power phase during which the heart rate sensor is powered down and not detecting the heart rate of the user. The wearable electronic device may further include a processor configured to run a heart rate estimation module being configured to calculate an estimated heart rate of the user based upon the motion of the user detected from the motion sensor during the low power phase and based upon the correspondence between the heart rate of the user and the motion of the user determined in the initial calibration phase.

Figure 1A:
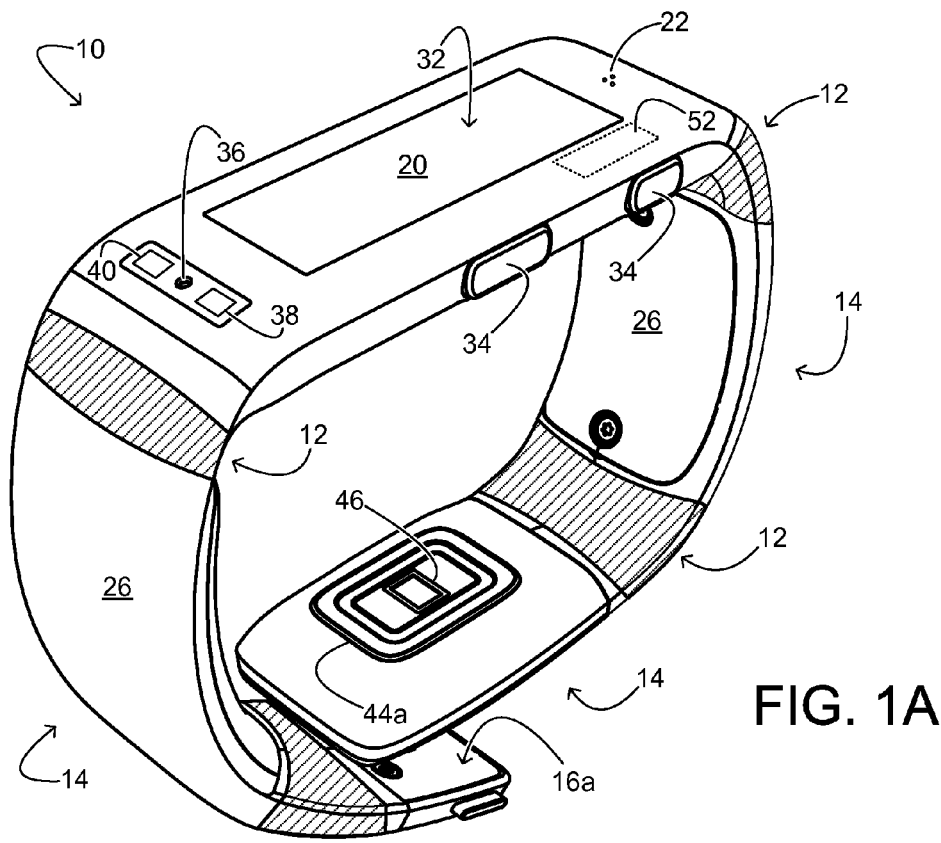
FIGS. 1A and 1B are top and bottom perspective views that show an example sensory-and-logic system in the form of a wearable electronic device.
Figure 1B:
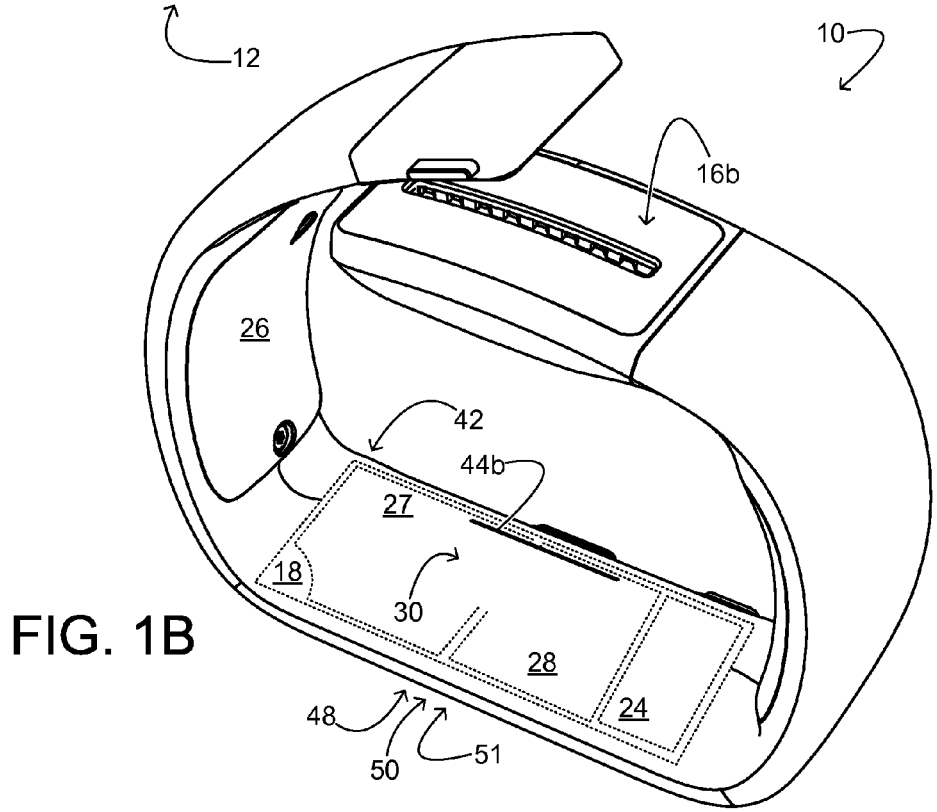

A sensory-and-logic system in the form of a wearable electronic device 10 is shown in FIGS. 1A and 1B. The illustrated device 10 is band-shaped and may be worn around a wrist. Device 10 includes at least four flexion regions 12 linking less flexible regions 14. The flexion regions of device 10 may be elastomeric in some examples. Fastening componentry 16A and 16B is arranged at both ends of the device. The flexion regions and fastening componentry enable the device to be closed into a loop and to be worn on a user's wrist. In other implementations, wearable electronic devices of a more elongate band shape may be worn around the user's bicep, waist, chest, ankle, leg, head, or other body part. The device, for example, may take the form of eye glasses, a head band, an arm-band, an ankle band, a chest strap, or an implantable device to be implanted in tissue.

Wearable electronic device 10 includes various functional components integrated into regions 14. In particular, the electronic device includes a compute system 18, display 20, loudspeaker 22, communication suite 24, and various sensors. These components draw power from one or more energy-storage cells 26. A battery—e.g., a lithium ion battery—is one type of energy-storage cell suitable for this purpose. Examples of alternative energy-storage cells include super- and ultra-capacitors. In devices worn on the user's wrist, the energy-storage cells may be curved to fit the wrist, as shown in the drawings.

In general, energy-storage cells 26 may be replaceable and/or rechargeable. In some examples, recharge power may be provided through a universal serial bus (USB) port 30, which includes a magnetic latch to releasably secure a complementary USB connector. In other examples, the energy storage cells may be recharged by wireless inductive or ambient-light charging. In still other examples, the wearable electronic device may include electro-mechanical componentry to recharge the energy storage cells from the user's adventitious or purposeful body motion. For example, batteries or capacitors may be charged via an electromechanical generator integrated into device 10. The generator may be turned by a mechanical armature that turns while the user is moving and wearing device 10.

In wearable electronic device 10, compute system 18 is situated below display 20 and operatively coupled to the display, along with loudspeaker 22, communication suite 24, and the various sensors. The compute system includes a data-storage machine 27 to hold data and instructions, and a logic machine 28 to execute the instructions. Aspects of the compute system are described in further detail with reference to FIG. 4.

Display 20 may be any suitable type of display. In some configurations, a thin, low-power light emitting diode (LED) array or a liquid-crystal display (LCD) array may be used. An LCD array may be backlit in some implementations. In other implementations, a reflective LCD array (e.g., a liquid crystal on silicon, LCOS array) may be frontlit via ambient light. A curved display may also be used. Further, AMOLED displays or quantum dot displays may be used.

Communication suite 24 may include any appropriate wired or wireless communications componentry. In FIGS. 1A and 1B, the communications suite includes USB port 30, which may be used for exchanging data between wearable electronic device 10 and other computer systems, as well as providing recharge power. The communication suite may further include two-way Bluetooth, Wi-Fi, cellular, near-field communication and/or other radios. In some implementations, the communication suite may include an additional transceiver for optical, line-of-sight (e.g., infrared) communication.

In wearable electronic device 10, touch-screen sensor 32 is coupled to display 20 and configured to receive touch input from the user. The touch sensor may be resistive, capacitive, or optically based. Pushbutton sensors may be used to detect the state of push buttons 34, which may include rockers. Input from the pushbutton sensors may be used to enact a home-key or on-off feature, control audio volume, turn the microphone on or off, or another function.

FIGS. 1A and 1B show various other sensors of wearable electronic device 10. Such sensors include microphone 36, visible-light sensor 38, ultraviolet sensor 40, and ambient temperature sensor 42. The microphone provides input to compute system 18 that may be used to measure the ambient sound level or receive voice commands from the wearer. Input from the visible-light sensor, ultraviolet sensor, and ambient temperature sensor may be used to assess aspects of the wearer's environment—i.e., the temperature, overall lighting level, and whether the wearer is indoors or outdoors.

FIGS. 1A and 1B show a pair of contact sensor modules 44A and 44B, which contact the wearer's skin when wearable electronic device 10 is worn. The contact sensor modules may include independent or cooperating sensor elements, to provide a plurality of sensory functions. For example, the contact sensor modules may provide an electrical resistance and/or capacitance sensory function, which measures the electrical resistance and/or capacitance of the wearer's skin. Compute system 18 may use such input to assess whether or not the device is being worn, for instance. In some implementations, the sensory function may be used to determine how tightly the wearable electronic device is being worn. In the illustrated configuration, the separation between the two contact-sensor modules provides a relatively long electrical path length, for more accurate measurement of skin resistance. In some examples, a contact sensor module may also provide measurement of the wearer's skin temperature. Arranged inside contact sensor module 44A in the illustrated configuration is an optical pulse rate sensor 46. The optical pulse-rate sensor may include an LED emitter and matched photodiode to detect blood flow through the capillaries in the skin and thereby provide a measurement of the wearer's pulse rate.

Wearable electronic device 10 may also include motion sensing componentry, such as an accelerometer 48, gyroscope 50, and magnetometer 51. The accelerometer and gyroscope may furnish inertial and/or rotation rate data along three orthogonal axes as well as rotational data about the three axes, for a combined six degrees of freedom. This sensory data can be used to provide a pedometer/calorie-counting function, for example. Data from the accelerometer and gyroscope may be combined with geomagnetic data from the magnetometer to further define the inertial and rotational data in terms of geographic orientation. The wearable electronic device may also include a global positioning system (GPS) receiver 52 for determining the wearer's geographic location and/or velocity. In some configurations, the antenna of the GPS receiver may be relatively flexible and extend into flexion regions 12.

Compute system 18, via the sensory functions described herein, is configured to acquire various forms of information about the wearer of wearable electronic device 10. Such information must be acquired and used with utmost respect for the wearer's privacy. Accordingly, the sensory functions may be enacted subject to opt-in participation of the wearer. In implementations where personal data is collected on the device and transmitted to a remote system for processing, that data may be anonymized. In other examples, personal data may be confined to the wearable electronic device, and only non-personal, summary data transmitted to the remote system.

Figure 2B:
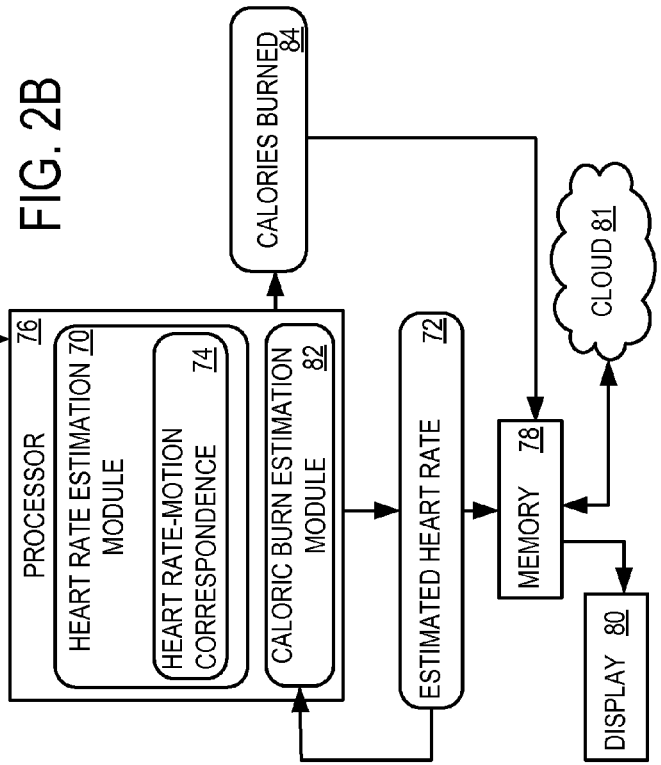
FIGS. 2A and 2B show the operation of a heart monitoring estimation module of the wearable electronic device of FIG. 1 in an initial calibration phase and a low power phase, respectively.
Figure 2A:
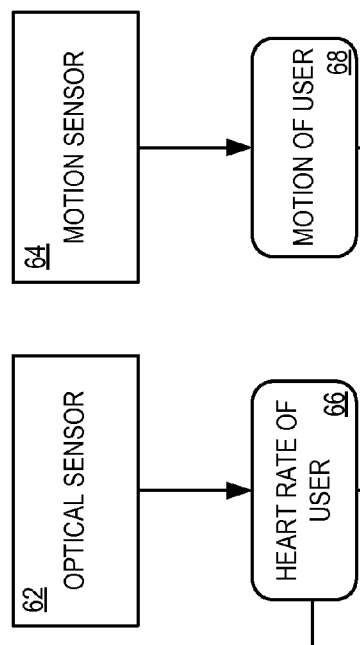

In some embodiments, the wearable electronic device described above may be used to monitor the heart rate of a user. FIGS. 2A and 2B show the operation of a heart rate estimation module 70 of the wearable electronic device 10 in an initial calibration phase and a low power phase, respectively. The wearable electronic device 10 may comprise a heart rate sensor to determine a heart rate of the user 66 and a motion sensor 64 configured to detect motion of a user 68. In the depicted example, the heart rate sensor is shown as optical sensor 62 which may be configured to emit light to the skin of a user and detect changes in reflected light. The motion sensor 64 may be operated in an initial calibration phase (as depicted in FIG. 2A) during which the optical sensor 62 is powered and detecting the heart rate of the user 66, and the motion sensor 64 is detecting motion of the user 68. The initial calibration phase may be used to compute a correspondence 74 between motion of the user 68 and the heart rate of the user 66. The motion sensor 64 may be further operated in a low power phase (depicted in FIG. 2B) during which the optical sensor 62 is powered down and not detecting the heart rate of the user 66. A processor 76 may be configured to run a heart rate estimation module 70. The heart rate estimation module 70 may be configured to calculate an estimated heart rate 72 of the user based upon the motion of the user 68 detected from the motion sensor 64 during the low power phase and based upon the correspondence 74 between the heart rate of the user 66 and the motion of the user 68 determined in the initial calibration phase.

FIG. 2A depicts the operation of the heart rate estimation module 70 in the initial calibration phase. In the initial calibration phase, the wearable electronic device 10 may be configured to detect the heart rate of the user 66 and the motion of the user 68 via optical sensor 62 and motion sensor 64, respectively. Optical sensor 62 and motion sensor 64 may respectively be optical pulse rate sensor 46 and accelerometer 48, gyroscope 50, or magnetometer 51.

The wearable electronic device 10 may be further configured to send the heart rate of the user 66 and the motion of the user 68 to the heart rate estimation module 70. The heart rate estimation module 70 may be configured to run as a program on processor 76 of the wearable electronic device 10. The heart rate estimation module 70 may be configured to receive the heart rate of the user 66 and motion of the user 68 and, based on this data, compute a correspondence 74 between the heart rate of the user 66 and the motion of the user 68. In addition, the wearable electronic device may be further configured to send the heart rate of the user 66 to memory 78. The wearable electronic device 10 may then be further configured to send the heart rate of the user 66 to a display 80 so as to be viewable by a user.

FIG. 2B depicts the operation of the heart rate estimation module 70 in the low power phase. In the low power phase, the wearable electronic device 10 may be configured to power down the optical sensor 62 and therefore not detect the heart rate of the user 66. The wearable electronic device 10 may be further configured to detect the motion of the user 68 via the motion sensor 64 and send the motion of the user 68 to the heart rate estimation module 70. The heart rate estimation module 70 may then be configured to receive the motion of the user 68 and calculate an estimated heart rate 72. The heart rate estimation module may be configured to calculate the estimated heart rate 72 based on the correspondence 74 between the heart rate of the user 66 and the motion of the user 68 computed during the initial calibration phase described above.

The heart rate estimation module 70 may be further configured to send the estimated heart rate 72 to memory 78 and the wearable electronic device 10 may then be configured to send the estimated heart rate 72 to the display 80 so as to be viewable by the user.

The wearable electronic device 10 may be further configured to include a caloric burn estimation module 82. The caloric burn estimation module 82 may be configured to compute calories burned 84 at least partially based on the estimated heart rate 72 during the low power phase. As shown in FIGS. 2A and 2B, the caloric burn estimation module 82 may be configured to run as a program on processor 76 of the wearable electronic device 10. In the low power phase shown in FIG. 2B, the caloric burn estimation module may be further configured to receive the estimated heart rate 72 computed by the heart rate estimation module 70. The caloric burn estimation module 82 may be configured to calculate the number of calories burned 84 over a period of time based on the estimated heart rate 72 of the user over that period of time. The wearable electronic device 10 may be configured to send the number of calories burned 84 to memory 78 and may then be further configured to send the number of calories burned 84 to the display 80 so as to be viewable by the user.

In the initial calibration phase shown in FIG. 2A, the caloric burn estimation module 82 may be configured to receive the heart rate of the user 66 from the optical sensor 62. The caloric burn estimation module 82 may then be configured to calculate a number of calories burned 84 over a period of time based on the heart rate of the user 66 over that period of time. The wearable electronic device 10 may be configured to send the number of calories burned 84 to memory 78 and may then be further configured to send the number of calories burned 84 to the display 80 so as to be viewable by the user.

As stated above, the processor 76 may be further configured to display the calories burned on a display 80 of the wearable electronic device 10. During both the initial calibration phase and the low power phase, as depicted in FIGS. 2A and 2B, respectively, the wearable electronic device 10 may be configured to display the number of calories burned 84 on the display 80 so as to be viewable by the user. The wearable electronic device 10 may be further configured to indicate to the user via the display 80 whether the number of calories burned is based on the estimated heart rate 72 or the heart rate of the user 66. The wearable electronic device 10 may be configured to display the number of calories burned 84 in a graphical form such as a line graph displaying the calories burned on one axis and time on the other axis. Such a graphical display may be further configured to display (e.g. with dashed lines, etc.) which portion of the graph were computed based on the estimated heart rate 72 of the user and which portions were computed based on the heart rate of the user 66.

The wearable electronic device 10 may be configured as a wearable computing device and the processor 76, optical sensor 62, and motion sensor 64 are mounted thereto. Turning briefly back to FIGS. 1A and 1B, and as discussed above, the wearable electronic device 10 may be configured as a wearable computing system in the form of a wristband, watch, or other suitable device such as an ankle-band, foot/shoe sensor, or torso sensor. The processor 76 may be incorporated into compute system 18. Optical sensor 62 and motion sensor 64, as stated above, may be optical pulse rate sensor 46 and accelerometer 48, gyroscope 50, or magnetometer 51.

The wearable electronic device 10 may be further configured such that the processor 76 operates in a remote mode in which the motion sensor 64 is a remote sensor in a remote device. The processor 76 may then be further configured to receive remote data from the remote sensor and compute the estimated heart rate 72 based on the remote data. The processor 76 may be further configured to operate the heart rate estimation module 70 in a remote mode in which motion sensor 64 is a remote sensor in a remote device connected by the cloud 81. The processor 76 may be configured to receive motion of the user 68 as remote data from the remote sensor and compute the estimated heart rate 72 in the low power phase based on the remote data. For example, the remote device may be a smartphone in the user's hand or pocket. In such a configuration, the wearable electronic device 10 may perform the same operations as in the low power phase by receiving remote data from the remote device over Wi-Fi or Bluetooth, for example, without powering the motion sensor 64, itself. In other embodiments, the processor 76 may be the processor of a mobile phone, PC, or other suitable device configured to run the heart rate estimation module 70, and the processor 76 may then be configured to receive remote data from the remote sensor and compute the estimated heart rate 72 based on the remote data.

Figure 3:
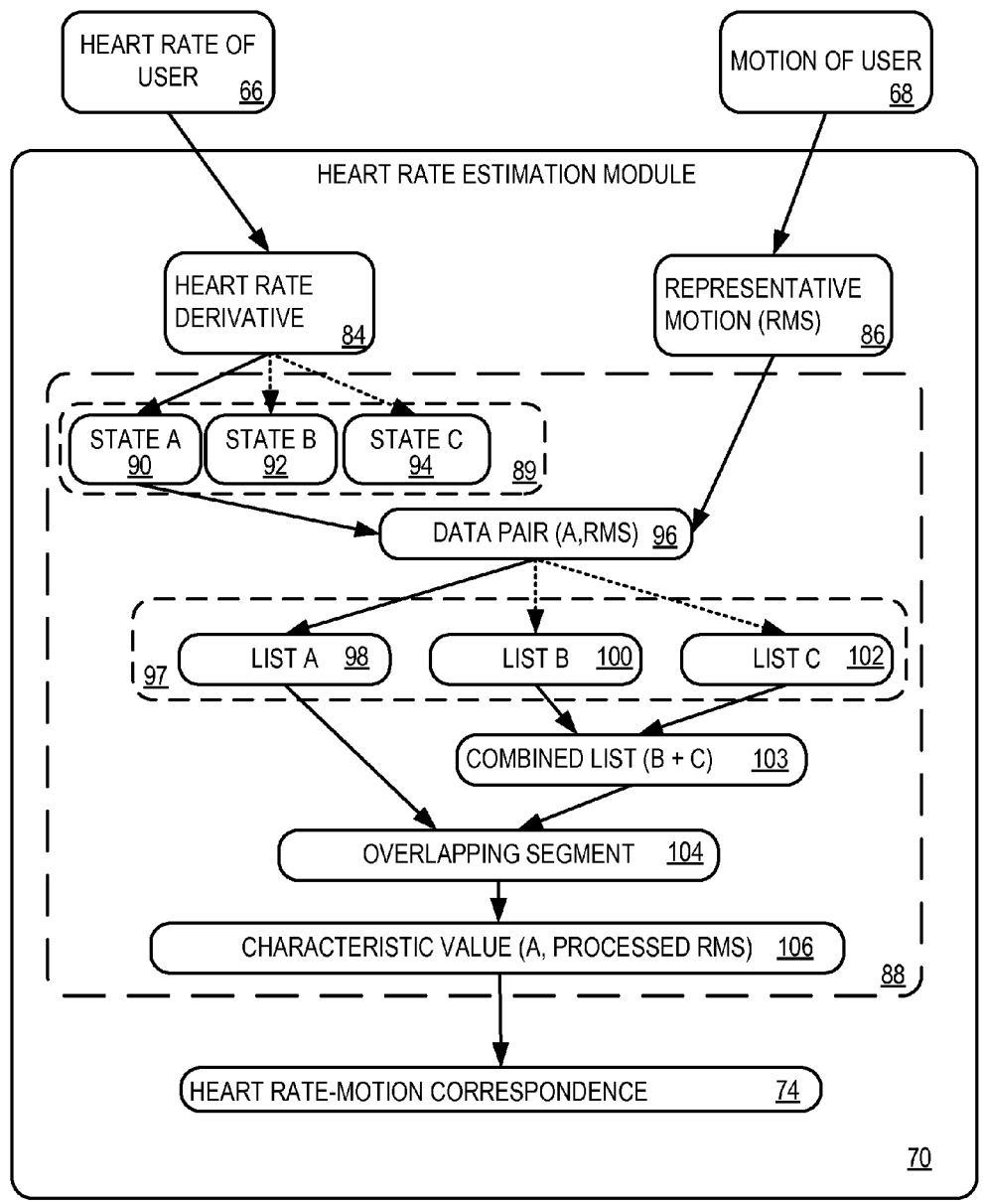
FIG. 3 shows an illustration of a statistical filter applied by the heart rate estimation module during the initial calibration phase of FIG. 2A to compute a correspondence between a heart rate of the user and motion of the user.

Turning next to FIG. 3, an illustration of a statistical filter 88 applied by the heart rate estimation module 70 of FIGS. 2A and 2B to compute a correspondence 74 between the heart rate of the user 66 and motion of the user 68 is depicted. The heart rate estimation module 70 may be further configured to calculate a heart rate derivative 84 with respect to time and a representative motion value 86 for each of a plurality of intervals during the initial calibration phase. The heart rate estimation module 70 may then be further configured to apply a statistical filter 88 to the heart rate derivatives 84 and the representative motion values 86 calculated in the initial calibration phase in order to compute a correspondence 74 between the heart rate of the user 66 and the motion of the user 68. As shown in FIG. 3, the heart rate estimation module 70 may be configured to receive the heart rate of the user 66 and the motion of the user 68 during the initial calibration phase. The heart rate estimation module 70 may then be configured to calculate a heart rate derivative 84 and a representative motion value 86. The representative motion value 86 may be any suitable representation of the data values over the interval of time, such as a root-mean-square, average, median, mode, integral (sum), or other meta-characteristic found through functional regression. Such an interval may be any suitable length of time such as, for example, 1 second. It should be noted that FIG. 3 depicts only a single instance of such a calculation; however, the operation depicted in FIG. 3 may be repeated so as to calculate the heart rate derivative 84 and the representative motion value 86 for a plurality of intervals over a period of time.

The heart rate estimation module 70 may then be configured to apply the statistical filter 88 to the heart rate derivative 84 and the representative motion value 86 in order to calculate the heart rate-motion correspondence 74. The statistical filter 88 may be further configured to classify each heart rate derivative 84 into one of a plurality of quantized derivative states 89. The statistical filter 84 may be further configured to sort the representative motion values 86 into a plurality of lists 97 based on the quantized derivative state of the heart rate derivative 84 associated with each representative motion value 86. The statistical filter 88 may then be further configured to compare the representative motion values 86 in each list 97 to the representative motion values 86 in every other list in order to identify an overlapping segment 104 in each list 97. The statistical filter 88 may then be configured to compute a characteristic value 106 for each list 97 by processing the representative motion values 86 in the overlapping segment 104 for each list 97. Processing the representative motion values may include taking an average or median of the values. The statistical filter 88 may be configured such that when it receives the heart rate derivative 84 and the representative motion value 86 from the heart rate estimation module 70, it classifies the heart rate derivative 84 into one of a plurality of quantized heart rate derivate states 89. FIG. 3 shows three quantized derivative states 89: State A 90, State B 92, and State C 94. In other embodiments, there may be more or fewer quantized derivative states 89 without changing the functionality of the statistical filter 88. The quantized derivate states 89 may represent ranges of the possible heart rate derivative 84. For example, the quantized derivative states 89 may be 1, 0, and −1. As such, when the heart rate of the user 66 is not changing significantly and thus the heart rate derivative 84 is within a predetermined threshold value of 0, the heart rate derivative 84 will be classified into the 0 state. When the heart rate of the user 66 is increasing and thus the heart rate derivative 84 is above the threshold value, the heart rate derivative 84 may be classified into the 1 state. Finally, when the heart rate of the user 66 is decreasing and thus the heart rate derivative 84 is below the threshold value, the heart rate derivative 84 will be classified into the −1 state.

After classifying the heart rate derivative 84 into one of the plurality of quantized derivative states 89, the statistical filter 88 may then be configured to construct a data pair 96 consisting of the quantized derivative state 89 of the heart rate derivative 84 and the representative motion value 86 corresponding to that period of time. In FIG. 3, the heart rate derivative 84 is classified into State A 90 and the data pair thus includes State A 90 and the representative motion value 86 of the user. The data pair 96 may then be sorted into one of a plurality of lists 97 based on the value of the quantized derivative state 89. FIG. 3 shows three lists 97: List A 98, List B 100, and List C 102. In other embodiments, there may be more or fewer lists 97 without changing the functionality of the statistical filter 88 as long as the number of lists 97 is equal to the number of quantized derivative states 89. The lists 97 may each be sorted in ascending order based on the representative motion value 86 of each data pair 96.

In FIG. 3, the data pair 96 is sorted into List A 98. The statistical filter 88 may be then configured to compare a single list, such as List A 98, to the other lists in the plurality of lists 97. The statistical filter 88 may be configured to create a combined list 103 by combining all the lists other than List A 96. The statistical filter 88 may then be configured to identify an overlapping segment 104. The overlapping segment 104 may consist of all data pairs 96 in List A 98 in which the representative motion value 86 is within a range defined by the largest and/or smallest representative motion value 86 in the combined list 103. The statistical filter 88 may be configured to identify the overlapping segment so as to eliminate outlier values that do not properly represent a relationship between the motion of the user 68 and the heart rate of the user 66. For example, if a user has been sitting perfectly still on a chair for an extended period of time, the user's heart rate is very likely not changing. If the user then raises an arm quickly, a high level of motion will be recorded but the heart rate will likely not be affected by such a brief motion. Such a data pair, when compared to other data pairs over time, may be considered an outlier that would distort an otherwise consistent relationship between motion and heart rate. Identifying an overlapping segment 104 of a single list (i.e. List A 98) to the combined list 103 may help remove such outliers from the data set.

The statistical filter 88 may then be configured to calculate a characteristic value 106 from the overlapping segment 104, for List A 98. The heart rate estimation module 70 may be configured to repeat this process for each list in the plurality of lists 97 until a characteristic value 106 has been determined for each list 97. The heart rate estimation module 70 may then be configured to define the heart rate-motion correspondence 74 based on these characteristic values 106.

Figure 4:
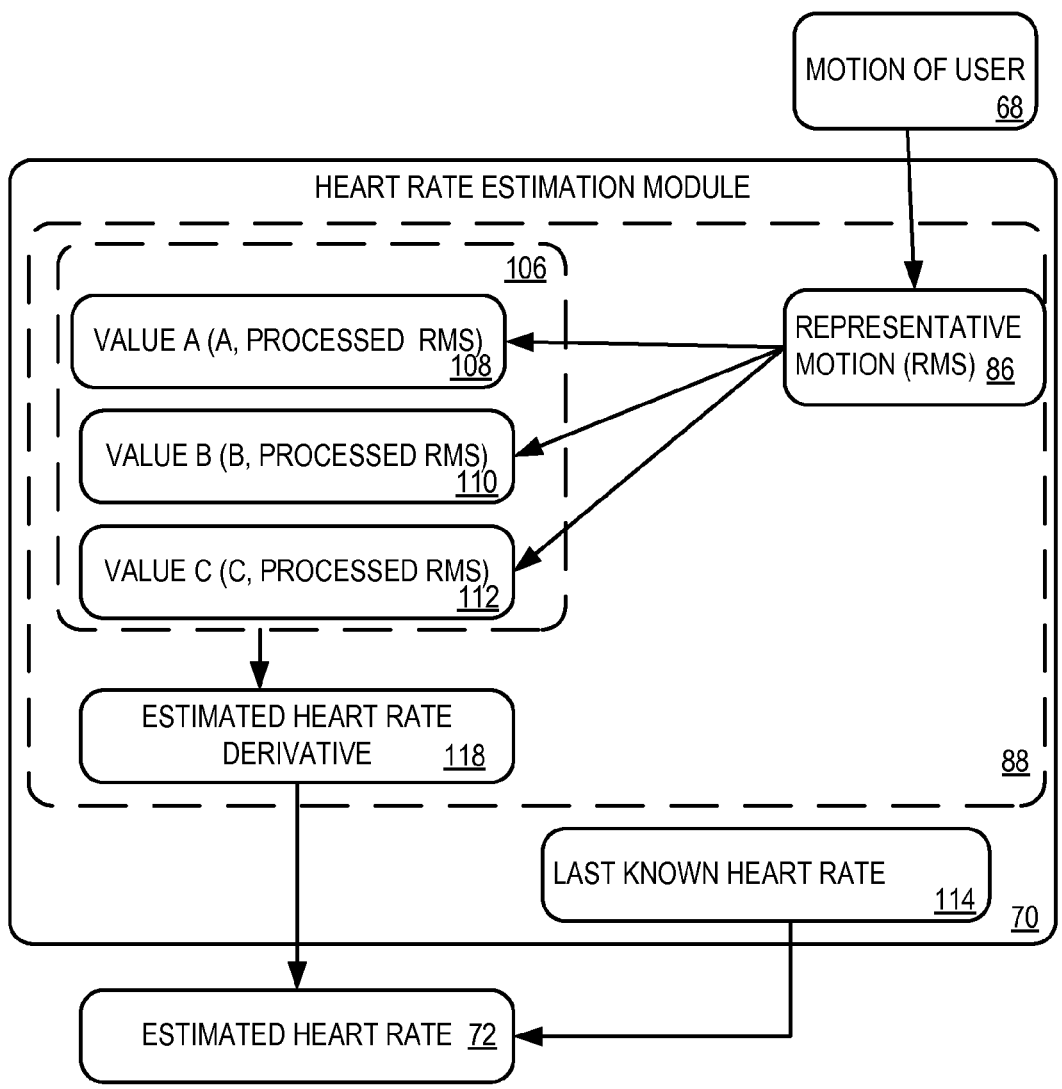
FIG. 4 shows an illustration of a statistical filter applied by the heart rate estimation module during the low power phase of FIG. 2B to compute an estimated heart rate.

Turning next to FIG. 4, the heart rate estimation module 70 may be further configured to apply the statistical filter 88 during the low power phase to determine an estimated heart rate 72 of the user by calculating a representative motion value 86 for each of a plurality of intervals during the low power phase, comparing the representative motion value 86 to the characteristic value 106 for each of the quantized derivative states 89, calculating an estimated heart rate derivative 118 based on the characteristic values 106, and computing the estimated heart rate 72 based on a last known heart rate 114 and the estimated heart rate derivative 118. In the low power phase, the heart rate estimation module 70 may be configured to receive the motion of the user 68 from the motion sensor 64. The statistical filter 88 may then be configured to calculate a representative motion value 86 from the motion of the user 68. FIG. 4 shows one instance of such a calculation. However, it should be noted that the heart rate estimation module 70 may be configured to calculate a representative motion value 86 for a plurality of intervals over time.

The heart rate estimation module 70 may then be configured to compare the representative motion value 86 to each of the characteristic values 106 calculated during the initial calibration phase. In FIG. 4, three characteristic values are shown: Value A 108, Value B 110, and Value C 112. In other embodiments, the number of characteristic values 106 may be increased or decreased in order to equal the number of lists 97. The statistical filter 88 may be next configured to calculate an estimated heart rate derivative for the representative motion value 86 based on the characteristic values 106. The statistical filter 88 may also be configured to define a function based on the characteristic values 106 and calculate the estimated heart rate derivative 118 based on such a function. The statistical filter may then be configured to calculate an estimated heart rate 72 based on the estimated heart rate derivative 118 and the last known heart rate 114. The last known heart rate 114 may be the last measurement of the heart rate of the user 66 taken during the initial calibration phase. In other embodiments, the last known heart rate 114 may be a function of the heart rate taken over a period of time including both the heart rate of the user 66 taken during the initial calibration phase and estimated heart rate 72 taken during prior intervals of the low power phase.

The statistical filter 88 may be configured to be an Unscented Kalman Filter. The Unscented Kalman Filter may be configured to function in the following manner. The Unscented Kalman Filter creates an underlying mathematical state estimation model and operates on a two element state-space representation, where both the heart rate of the user 66 and the heart rate derivative 84 are the two elements. There are two primary interactions with the Unscented Kalman Filter, either using a data pair based on the heart rate of the user 66 and the motion of the user 68, or using just the motion of the user 68.

For the interaction using the data pair based on the heart rate of the user 66 and the motion of the user 68, the Unscented Kalman Filter is given a control input of the heart rate of the user 68 that biases the output to the measured signal having the effect of re-calibrating the outputs, but otherwise operates normally, to keep the error covariance matrices contiguous. The state apriori estimate is exactly equal to the control input (ignoring all feed-forward information from the last iteration's aposteriori estimate). This interaction also adds an entry in the appropriate list of the plurality of lists 97 used to estimate the heart rate derivative 84 given a representative motion value 86.

This interaction also performs a filtering operation to calculate an appropriate representative motion value 86 for each heart rate derivative quantization state 89 of the motion to derivative mapping, using the following algorithm for each quantization level. First, the recorded motion measurements are separated into two categories that represents motions causing a derivative greater than or equal to the quantization level (positive dataset) and less than or equal to the quantization level (negative dataset). For example, if the quantization level is a derivative of −1, the two lists will be the motions where the derivative was less than or equal to −1, and another list where the derivative is greater than or equal to −1. Second, both lists are sorted in ascending order. Third, an upper portion such as 50%-75% (the third quartile) of the data is selected from the negative data set, and a lower portion such as 25%-50% (the second quartile) of the data from the positive data set. Fourth, the intersection of the two selections from the previous step is found, by finding all values in the selected negative data set that are greater than the smallest value in the selected positive data set, and by finding all values in the selected positive data set that are less than the largest value in the selected negative data set. Fifth, the average or median value of the intersection data set is computed. If the intersection of the data contains no values, the average of the largest value in the selected negative data set and the smallest value in the selected positive data set is used. Finally, the result of this calculation is stored in a table with the quantization level (e.g. −1 bpm/s=x, 0 bpm/s=y, . . . , where x and y are the results of the algorithm for that quantization level).

For the motion only interaction, the Unscented Kalman Filter operates without a control input, and updates its state apriori model following the Equation 1 shown below.

coefficients for the specific application, and m is the representative motion value 86 assigned to time step k, which may be limited to a computation over time interval k−1 to k. The DerivativeEstimate(m) function used above is defined as the application of a functional regression of the filtered collected data pairs 96 of the heart rate derivative 84 and the representative motion value 86 onto the input motion parameter. For example, if the functional regression is chosen to be polynomial of rank 2 (i.e. a linear regression), then the DerivativeEstimate(m) will return the value a*m+b, where a and b are found through linear regression.

For all interactions, the Unscented Kalman Filter estimates the predicted measurement from the apriori state using the inverse of the regression that is used for the DerivativeEstimate function.

Figure 5A:
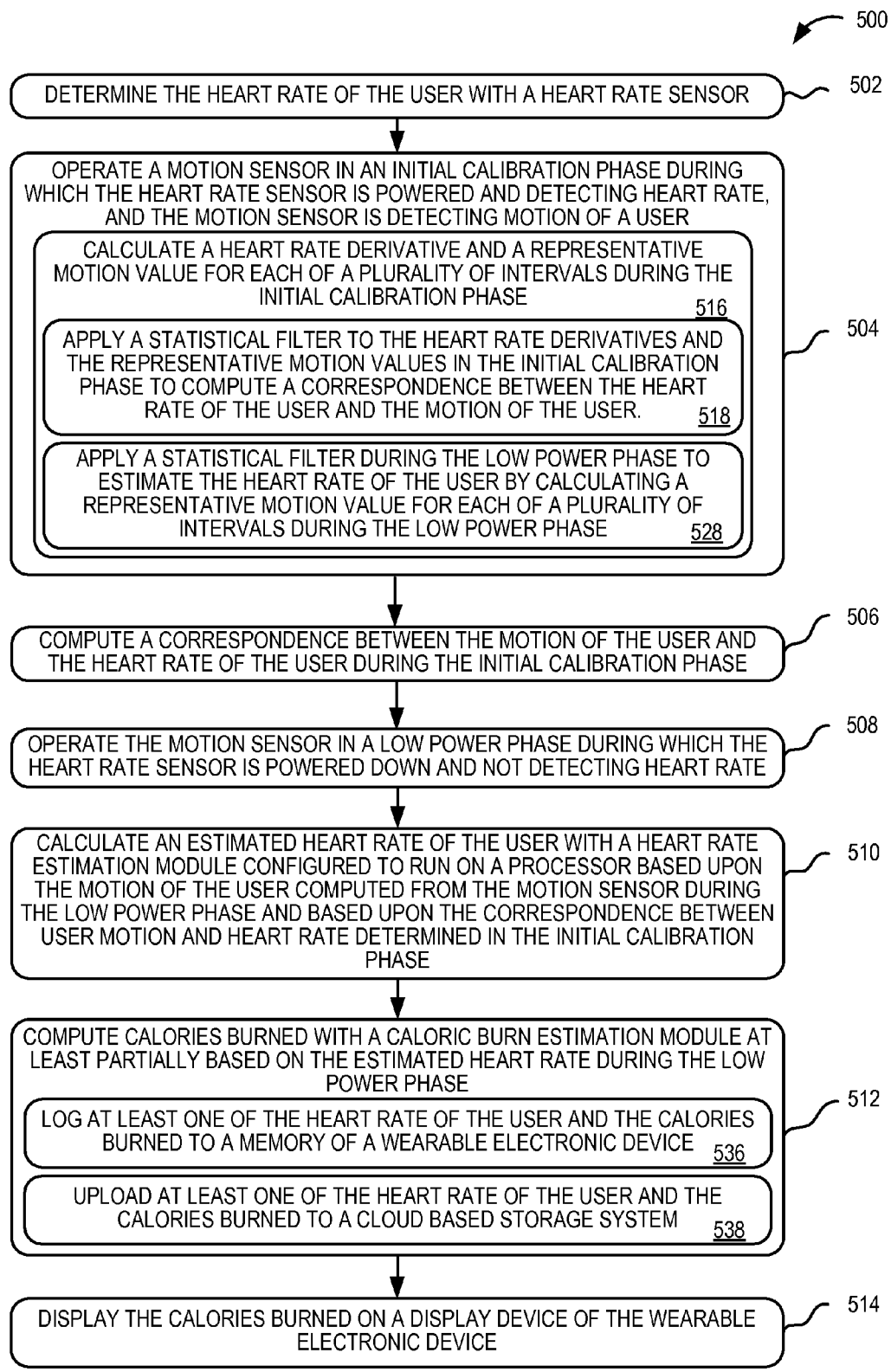
FIG. 5A is a flowchart of a method for estimating the heart rate of the user with the wearable electronic device.

Turning next to FIG. 5A, a method 500 for estimating the heart rate of the user with the wearable electronic device is depicted. At 502, the method 500 includes determining the heart rate of the user with an optical sensor. At 504, the method 500 includes operating a motion sensor in an initial calibration phase during which the optical sensor is powered and detecting heart rate, and the accelerometer is detecting motion of a user. At 506, the method 500 includes computing a correspondence between the motion of the user and the heart rate of the user during the initial calibration phase. At 508, the method 500 includes operating the motion sensor in a low power phase during which the optical sensor is powered down and not detecting heart rate. At 510, the method 500 includes calculating an estimate heart rate of the user with a heart rate estimation module configured to run on a processor based upon the motion of the user computed from the accelerometer during the low power phase and based upon the correspondence between user motion and heart rate determined in the initial calibration phase. At 512, the method 500 includes computing calories burned with a caloric burn estimation module at least partially based on the estimate heart rate during the low power phase. At 514, the method 500 includes displaying the calories burned on a display device of the wearable electronic device. At 536, the step 512 of the method 500 further includes logging at least one of the heart rate of the user and the calories burned to a memory of a wearable electronic device. At 538, the step 512 of the method 500 further includes uploading at least one of the heart rate of the user and the calories burned to a cloud based storage system.

At 516, the step 504 of the method 500 further includes calculating a heart rate derivative and a representative motion value for each of a plurality of intervals during the initial calibration phase. At 518, the step 516 of the method 500 further includes applying a statistical filter to the heart rate derivatives and the representative motion values in the initial calibration phase to compute a correspondence between the heart rate of the user and the motion of the user.

Figure 5B:
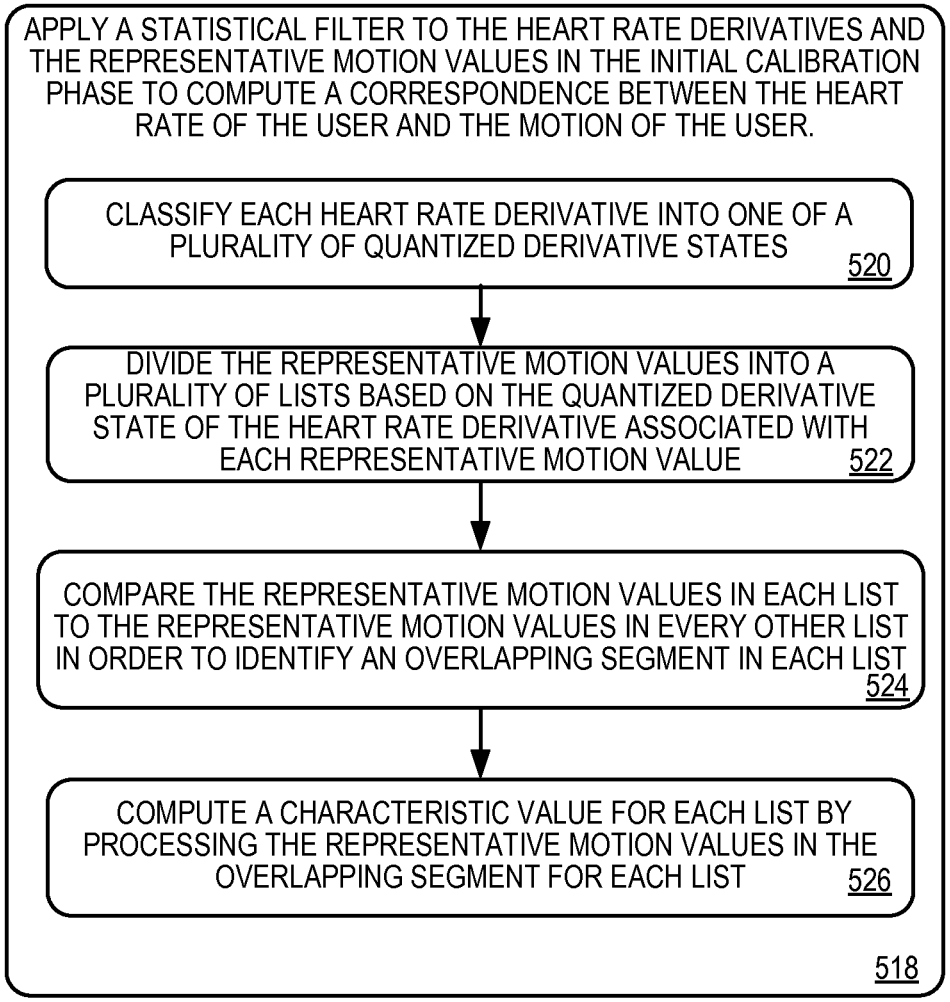
FIG. 5B is a flowchart of a method for achieving a step of the method of FIG. 5A.

FIG. 5B shows a method for achieving the step 518 of the method 500. At, 520 the step 518 includes classifying each heart rate derivative into one of a plurality of quantized $$\begin{bmatrix} HR \\ dHR/dt \end{bmatrix}_{k,apriori} = \begin{bmatrix} HR_{k-1,aposteriori} + dHR/dt_{k-1,aposteriori} * \alpha_3 \\ \alpha_1 * \alpha_2 * DerivativeEstimate(m_k) + (1 - \alpha_2) * dHR/dt_{k-1,aposteriori} \end{bmatrix}$$

Equation 1

In Equation 1 above, k indicates the current time step, k−1 is the previous time step, α values (1 through 3) are tuned derivative states. At 522, the step 518 includes dividing the representative motion values into a plurality of lists based on the quantized derivative state of the heart rate derivative associated with each representative motion value. At 524, the step 518 includes comparing the representative motion values in each list to the representative motion values in every other list in order to identify an overlapping segment in each list. At 526, the step 518 includes computing a characteristic value for each list by processing the representative motion values in the overlapping segment for each list.

Returning to FIG. 5A, the step 516 of the method 500 further includes, at 528, applying a statistical filter during the low power phase to estimate the heart rate of the user by calculating a representative motion value for each of a plurality of intervals during the low power phase.

Figure 5C:
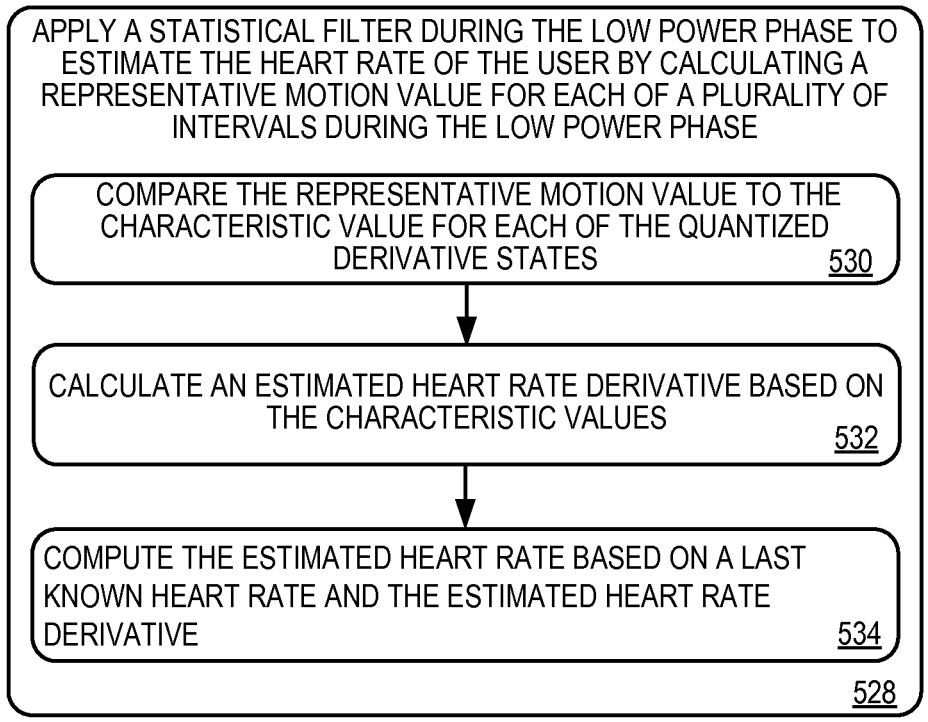
FIG. 5C is a flowchart of a method for achieving a step of the method of FIG. 5A.

FIG. 5C shows a method for achieving the step 528 of the method 500. At 530, the step 528 includes comparing the representative motion value to the characteristic value 106 for each of the quantized derivative states. At 532, the step 528 includes selecting one of the plurality of quantized derivative states corresponding to the representative motion value. At 534, the step 528 includes computing the estimated heart rate based on a last known heart rate and the quantized derivative state.

It should also be noted that, while the methods and system described above employ an optical sensor as the heart rate sensor to measure the heart rate of a user, any suitable sensor for accurately measuring a user's heart rate, such as capacitance, impedance, pressure, and/or ultrasound sensors to determine the heart rate of the user, could be used.

In addition, although the depicted embodiments described above show a device used to correlate the heart rate of a user and the motion level of the user, it should be understood that the methods disclosed herein are not limited to computing a correspondence between heart rate and motion. Rather, the methods described above may be used to achieve proxy-measurements for a wide range of other loosely coupled signals, including suitable biometric factors of a user.

As such, according to another aspect of the invention, the device may comprise a first sensor configured to determine a first biometric factor of the user and a second sensor configured to detect a second biometric factor of the user. The second sensor may be configured to operate in an initial calibration phase during which the first sensor is powered and detecting the first biometric factor and the second sensor is detecting the second biometric factor. The calibration phase may be used to compute a correspondence between the first biometric factor and the second biometric factor. The second sensor may be operated in a low power phase during which the first sensor is powered down and not detecting the first biometric factor. The device may further comprise a processor configured to run an estimation module configured to calculate an estimated first biometric factor of the user based upon the detected second biometric factor from the second sensor during the low power phase and based upon the correspondence between the first biometric factor of the user and the second biometric factor of the user determined in the initial calibration phase. The processor may be configured to output the estimated second biometric factor on a display associated with the computing system, or to further compute a value that is a function of the estimated second biometric factor, such as caloric burn discussed above, and display the value on the display associated with the computing system. In addition, the processor may be configured to log the first biometric factor, the estimated second biometric, or both to a memory associated with the computing system, and may be further configured to upload the first biometric factor, the estimated second biometric factor, or both, to a cloud-based storage system associated with the computing system.

As evident from the foregoing description, the methods and processes described herein may be tied to a sensory-and-logic system of one or more machines. Such methods and processes may be implemented as a computer-application program or service, an application-programming interface (API), a library, firmware, and/or other computer-program product. FIGS. 1A and 1B show one, non-limiting example of a sensory-and-logic system to enact the methods and processes described herein. However, these methods and process may also be enacted on sensory-and-logic systems of other configurations and form factors, as shown schematically in FIG. 6.

Figure 6:
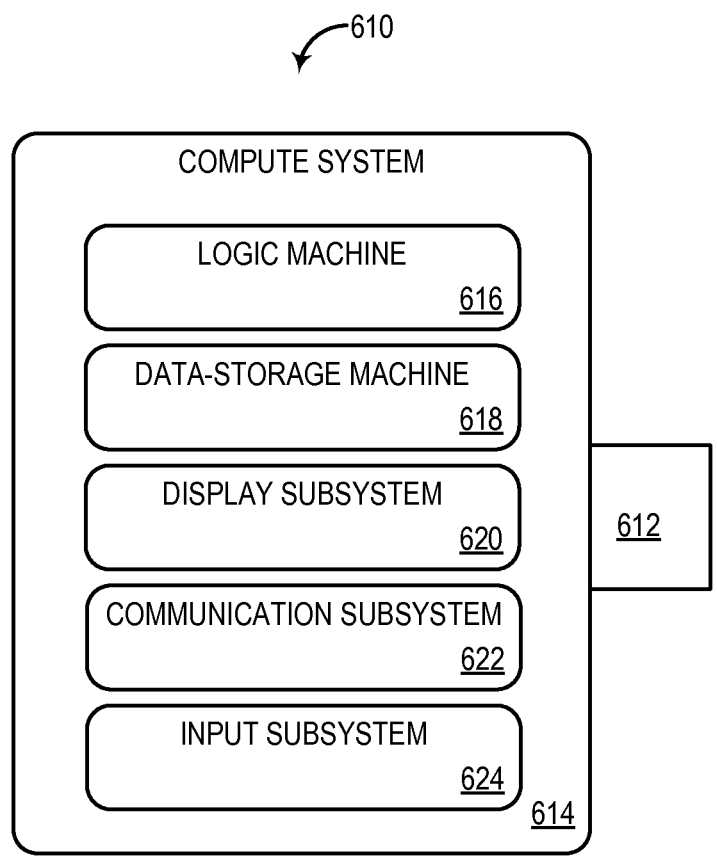
FIG. 6 shows a simplified schematic view of a compute system that may embody the sensory-and-logic system.

FIG. 6 schematically shows a form-agnostic sensory-and-logic system 610 that includes a sensor suite 612 operatively coupled to a compute system 614. The compute system includes a logic machine 616 and a data-storage machine 618. The compute system is operatively coupled to a display subsystem 620, a communication subsystem 622, an input subsystem 624, and/or other components not shown in FIG. 6.

Logic machine 616 includes one or more physical devices configured to execute instructions. The logic machine may be configured to execute instructions that are part of one or more applications, services, programs, routines, libraries, objects, components, data structures, or other logical constructs. Such instructions may be implemented to perform a task, implement a data type, transform the state of one or more components, achieve a technical effect, or otherwise arrive at a desired result.

Logic machine 616 may include one or more processors configured to execute software instructions. Additionally or alternatively, the logic machine may include one or more hardware or firmware logic machines configured to execute hardware or firmware instructions. Processors of the logic machine may be single-core or multi-core, and the instructions executed thereon may be configured for sequential, parallel, and/or distributed processing. Individual components of a logic machine optionally may be distributed among two or more separate devices, which may be remotely located and/or configured for coordinated processing. Aspects of a logic machine may be virtualized and executed by remotely accessible, networked computing devices in a cloud-computing configuration.

Data-storage machine 618 includes one or more physical devices configured to hold instructions executable by logic machine 616 to implement the methods and processes described herein. When such methods and processes are implemented, the state of the data-storage machine may be transformed—e.g., to hold different data. The data-storage machine may include removable and/or built-in devices; it may include optical memory (e.g., CD, DVD, HD-DVD, Blu-Ray Disc, etc.), semiconductor memory (e.g., RAM, EPROM, EEPROM, etc.), and/or magnetic memory (e.g., hard-disk drive, floppy-disk drive, tape drive, MRAM, etc.), among others. The data-storage machine may include volatile, nonvolatile, dynamic, static, read/write, read-only, random-access, sequential-access, location-addressable, file-addressable, and/or content-addressable devices.

It will be appreciated that data-storage machine 618 includes one or more physical devices. However, aspects of the instructions described herein alternatively may be propagated by a communication medium (e.g., an electromagnetic signal, an optical signal, etc.) that is not held by a physical device for a finite duration.

Aspects of logic machine 616 and data-storage machine 618 may be integrated together into one or more hardware-logic components. Such hardware-logic components may include field-programmable gate arrays (FPGAs), program- and application-specific integrated circuits (PASIC/ASICs), program- and application-specific standard products (PSSP/ASSPs), system-on-a-chip (SOC), and complex programmable logic devices (CPLDs), for example.

Display subsystem 620 may be used to present a visual representation of data held by data-storage machine 618. This visual representation may take the form of a graphical user interface (GUI). As the herein described methods and processes change the data held by the storage machine, and thus transform the state of the storage machine, the state of display subsystem 620 may likewise be transformed to visually represent changes in the underlying data. Display subsystem 620 may include one or more display subsystem devices utilizing virtually any type of technology. Such display subsystem devices may be combined with logic machine 616 and/or data-storage machine 618 in a shared enclosure, or such display subsystem devices may be peripheral display subsystem devices. Display 20 of FIGS. 1A and 1B is an example of display subsystem 620.

Communication subsystem 622 may be configured to communicatively couple compute system 614 to one or more other computing devices. The communication subsystem may include wired and/or wireless communication devices compatible with one or more different communication protocols. As non-limiting examples, the communication subsystem may be configured for communication via a wireless telephone network, a local- or wide-area network, and/or the Internet. Communication suite 24 of FIGS. 1A and 1B is an example of communication subsystem 622.

Input subsystem 624 may comprise or interface with one or more user-input devices such as a keyboard, mouse, touch screen, or game controller. In some embodiments, the input subsystem may comprise or interface with selected natural user input (NUI) componentry. Such componentry may be integrated or peripheral, and the transduction and/or processing of input actions may be handled on- or off-board. Example NUI componentry may include a microphone for speech and/or voice recognition; an infrared, color, stereoscopic, and/or depth camera for machine vision and/or gesture recognition; a head tracker, eye tracker, accelerometer, and/or gyroscope for motion detection and/or intent recognition; as well as electric-field sensing componentry for assessing brain activity. Touch screen sensor 32 and push buttons 34 of FIGS. 1A and 1B are examples of input subsystem 624.

Sensor suite 612 may include one or more different sensors—e.g., a touch-screen sensor, push-button sensor, microphone, visible-light sensor, ultraviolet sensor, ambient-temperature sensor, contact sensors, optical pulse-rate sensor, accelerometer, gyroscope, magnetometer, and/or GPS receiver—as described above with reference to FIGS. 1A and 1B.

It will be understood that the configurations and approaches described herein are exemplary in nature, and that these specific implementations or examples are not to be taken in a limiting sense, because numerous variations are feasible. The specific routines or methods described herein may represent one or more processing strategies. As such, various acts shown or described may be performed in the sequence shown or described, in other sequences, in parallel, or omitted.

The subject matter of this disclosure includes all novel and non-obvious combinations and sub-combinations of the various processes, systems and configurations, and other features, functions, acts, and/or properties disclosed herein, as well as any and all equivalents thereof.

The invention claimed is:

1. A wearable electronic device, comprising:
an energy storage device configured to provide power;
a heart rate sensor configured to determine a heart rate of a user while receiving power from the energy storage device when instructed by a processor; and
a motion sensor configured to detect motion of the user while receiving power from the energy storage device when instructed by the processor;
wherein the processor is configured to:
in an initial calibration phase having a plurality of intervals and implemented by the processor:
instruct the energy storage device to provide power to the motion sensor from the energy storage device to enable detection of motion of the user with the motion sensor;
instruct the energy storage device to provide power to the heart rate sensor from the energy storage device to enable heart rate detection of the user with the heart rate sensor;
calculate a heart rate derivative and a representative motion value for each of the plurality of intervals in the initial calibration phase, the heart rate derivative being a variable representing change in the heart rate of the user with respect to time; and
compute a correspondence between the heart rate of the user and the motion of the user using the heart rate derivative and the representative motion value;
in a low power phase subsequent to the initial calibration phase and implemented by the processor:
continue to instruct the energy storage device to provide power to the motion sensor from the energy storage device to enable detection of motion of the user with the motion sensor;
instruct the energy storage device to cease providing power to the heart rate sensor to discontinue detection of the heart rate of the user; and
execute a heart rate estimation module configured to calculate an estimated heart rate of the user based upon the motion of the user detected from the motion sensor during the low power phase and based upon the correspondence between the heart rate of the user and the motion of the user determined in the initial calibration phase.

2. The wearable electronic device of claim 1, wherein the processor executes a caloric burn estimation module configured to compute calories burned at least partially based on the estimated heart rate during the low power phase.

3. The wearable electronic device of claim 2, further comprising a display wherein the processor is further configured to instruct the display to display the calories burned.

4. The wearable electronic device of claim 1, wherein the wearable electronic device is a wearable computing device and the processor, heart rate sensor, and motion sensor are mounted thereto.

5. The wearable electronic device of claim 1, wherein the processor is further configured to:
apply a statistical filter to the heart rate derivatives and the representative motion values calculated in the initial calibration phase in order to compute a correspondence between the heart rate of the user and the motion of the user.

6. The wearable electronic device of claim 5, wherein the statistical filter is an Unscented Kalman Filter.

7. The wearable electronic device of claim 5, wherein the statistical filter is further configured to:
classify each heart rate derivative into one of a plurality of quantized derivative states;
sort the representative motion values into a plurality of lists based on the quantized derivative state of the heart rate derivative associated with each representative motion value;
compare the representative motion values in each list to the representative motion values in every other list in order to identify an overlapping segment in each list; and
compute a characteristic value for each list by processing the representative motion values in the overlapping segment for each list.

8. The wearable electronic device of claim 7, wherein the heart rate estimation module is further configured to, during the low power phase, determine the estimated heart rate of the user by calculating a low power phase representative motion value for each of a low power phase plurality of intervals, comparing the low power phase representative motion value to the characteristic value for each of the quantized derivative states, calculating an estimated heart rate derivative based on the characteristic values, and computing the estimated heart rate based on a last known heart rate and the estimated heart rate derivative.

9. A method of estimating a heart rate of a user, comprising:
at a processor:
determining a heart rate of the user with signals from a heart rate sensor;
in an initial calibration phase having a plurality of intervals and implemented by the processor:
operating an energy storage device configured to provide power to a motion sensor to enable detection of motion of the user;
operating the energy storage device configured to provide power to the heart rate sensor to enable detection of the heart rate of the user; and
computing a correspondence between the motion of the user and the heart rate of the user, where computing a correspondence between the motion of the user and the heart rate of the user includes calculating a heart rate derivative and a representative motion value for each of the plurality of intervals in the initial calibration phase;
in a low power phase subsequent to the initial calibration phase and implemented by the processor:
operating the energy storage device configured to provide power to the motion sensor to enable detection of motion of the user;
operating the energy storage device configured to provide power to cease providing power to the heart rate sensor to discontinue detection of the heart rate of the user; and
executing a heart rate estimation module to calculate an estimated heart rate of the user based upon the motion of the user detected from the motion sensor during the low power phase and based upon the correspondence between the motion of the user and the heart rate of the user determined in the initial calibration phase.

10. The method of claim 9, further comprising:
computing calories burned with a caloric burn estimation module, executed by the processor, at least partially based on the estimated heart rate during the low power phase.

11. The method of claim 10, further comprising:
displaying the calories burned on a display device of a wearable electronic device.

12. The method of claim 10, further comprising:
logging at least one of the heart rate of the user and the calories burned to a memory of a wearable electronic device; and
uploading at least one of the heart rate of the user and the calories burned to a cloud based storage system.

13. The method of claim 10, further comprising:
applying a statistical filter to the heart rate derivatives and the representative motion values during the initial calibration phase to compute a correspondence between the heart rate of the user and the motion of the user.

14. The method of claim 13, further comprising:
classifying each heart rate derivative into one of a plurality of quantized derivative states;
dividing the representative motion values into a plurality of lists based on the quantized derivative state of the heart rate derivative associated with each representative motion value;
comparing the representative motion values in each list to the representative motion values in every other list in order to identify an overlapping segment in each list;
computing a characteristic value for each of the values in the list by processing the representative motion values in the overlapping segment for each list.

15. The method of claim 14, further comprising:
applying the statistical filter during the low power phase to estimate the heart rate of the user by calculating a low power phase representative motion value for each of a low power phase plurality of intervals during the low power phase.

16. The method of claim 15, further comprising:
comparing the low power phase representative motion value to the characteristic value for each of the quantized derivative states, calculating an estimated heart rate derivative based on the characteristic values, and computing the estimated heart rate based on a last known heart rate and the estimated heart rate derivative.

17. The method of claim 13, wherein the statistical filter is an Unscented Kalman Filter.

18. An electronic device, comprising:
an energy storage device configured to provide power;
a first sensor configured to determine a first biometric factor of a user while receiving power from the energy storage device when instructed by a processor; and
a second sensor configured to detect a second biometric factor of the user while the second sensor receives power from the energy storage device when instructed by the processor;
wherein the processor, is configured to:
implement an initial calibration phase and a subsequent low power phase;
in the initial calibration phase:
instruct the energy storage device to provide power to the first sensor and the second sensor; and
compute a correspondence between the first biometric factor and the second biometric factor using a calculated derivative of the first biometric factor;

in the low power phase:
continue to instruct the energy storage device to provide power to the second sensor;
instruct the energy storage device to cease providing power to the first sensor to discontinue detection of the first biometric factor;
execute an estimation module configured to calculate an estimated first biometric factor of the user based upon the second biometric factor detected from the second sensor during the low power phase and based upon the correspondence between the first biometric factor of the user and the second biometric factor of the user determined in the initial calibration phase; and
operate a display of the electronic device to display the estimated first biometric factor.

19. A system comprising:
a wearable electronic device including at least an energy storage device configured to provide power and a heart rate sensor configured to determine a heart rate of a user while receiving power from the energy storage device when instructed by a processor; and
a remote device including at least a motion sensor configured to detect motion of the user;
wherein the processor is configured to:
in an initial calibration phase having a plurality of intervals and implemented by the processor:
instruct the energy storage device to provide power to the heart rate sensor from the energy storage device to enable heart rate detection of the user with the heart rate sensor;
receive remote data from the remote device including data from the motion sensor through a communication subsystem of the wearable device;
calculate a heart rate derivative and a representative motion value for each of the plurality of intervals in the initial calibration phase, the heart rate derivative being a variable representing change in the heart rate of the user with respect to time; and
compute a correspondence between the heart rate of the user and the motion of the user using the heart rate derivative and the representative motion value;
in a low power phase subsequent to the initial calibration phase and implemented by the processor:
instruct the energy storage device to cease providing power to the heart rate sensor to discontinue detection of the heart rate of the user;
receive remote data from the remote device including data from the motion sensor through the communication subsystem; and
execute a heart rate estimation module configured to calculate an estimated heart rate of the user based upon the motion of the user detected from the motion sensor during the low power phase and based upon the correspondence between the heart rate of the user and the motion of the user determined in the initial calibration phase;
wherein the heart rate estimation module is configured to calculate the estimated heart rate based on the remote data.

* * * * *